United States Patent
Matsubara

(10) Patent No.: US 11,061,214 B2
(45) Date of Patent: Jul. 13, 2021

(54) CELL OBSERVATION APPARATUS AND METHOD

(71) Applicant: FUJIFILM Corporation, Tokyo (JP)

(72) Inventor: Kenta Matsubara, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 141 days.

(21) Appl. No.: 16/059,580

(22) Filed: Aug. 9, 2018

(65) Prior Publication Data

US 2018/0348493 A1   Dec. 6, 2018

Related U.S. Application Data

(63) Continuation of application No. PCT/JP2016/086085, filed on Dec. 5, 2016.

(30) Foreign Application Priority Data

Feb. 29, 2016 (JP) .............................. JP2016-037697

(51) Int. Cl.
*G02B 21/00* (2006.01)
*G02B 21/36* (2006.01)
(Continued)

(52) U.S. Cl.
CPC ......... *G02B 21/0056* (2013.01); *C12M 41/36* (2013.01); *C12M 41/46* (2013.01);
(Continued)

(58) Field of Classification Search
CPC ......... G01B 11/24; G01C 3/06; G01S 7/4863; G01S 17/42; G01S 17/89; H01L 27/148;
(Continued)

(56) References Cited

U.S. PATENT DOCUMENTS 9,041,793 B2 * 5/2015 Bugge .................. H01J 37/265
348/79
2003/0227673 A1   12/2003 Nakagawa
(Continued)

FOREIGN PATENT DOCUMENTS

DE   10235656 A1   2/2004
EP   2381287 A1 * 10/2011 ........... G02B 21/367
(Continued)

OTHER PUBLICATIONS

Korean Notification of Reason for Refusal for corresponding Korean Application No. 10-2018-7023737, dated May 8, 2019, with English translation.
(Continued)

*Primary Examiner* — Peet Dhillon
(74) *Attorney, Agent, or Firm* — Birch, Stewart, Kolasch & Birch, LLP

(57) ABSTRACT

A cell observation apparatus includes an image formation optical system control unit 51 which sets an initial scanning range of the focal position based on information relating to a thickness of a cell, forms an image of the cell at each of a plurality of focal positions within a set initial scanning range, subsequently acquires an image captured by an imaging unit 40 for each of the plurality of focal positions, estimates the thickness of the cell based on the image, updates the initial scanning range of the focal position based on the estimated thickness of the cell, and forms an image of the cell at each of a plurality of focal positions within the updated scanning range.

21 Claims, 5 Drawing Sheets

(51) Int. Cl.
*C12M 1/34* (2006.01)
*G02B 7/36* (2021.01)
*G02B 21/14* (2006.01)
*G02B 21/24* (2006.01)

(52) U.S. Cl.
CPC .............. *G02B 7/36* (2013.01); *G02B 21/14* (2013.01); *G02B 21/244* (2013.01); *G02B 21/361* (2013.01); *G02B 21/367* (2013.01)

(58) Field of Classification Search
CPC .... H04N 5/2352; H04N 5/33; H04N 5/36965; H04N 5/372; H04N 5/3728
See application file for complete search history.

(56) References Cited

U.S. PATENT DOCUMENTS

| | | | |
|---|---|---|---|
| 2004/0109169 A1 | 6/2004 | Olschewski | |
| 2009/0097734 A1* | 4/2009 | Fukuda | G01B 11/0625 382/133 |
| 2012/0236120 A1 | 9/2012 | Kramer et al. | |
| 2013/0279788 A1* | 10/2013 | Zahniser | G01N 15/0227 382/134 |
| 2014/0232844 A1 | 8/2014 | Wolff et al. | |
| 2016/0369223 A1 | 12/2016 | Matsumoto | |
| 2017/0003490 A1* | 1/2017 | Sueki | G06T 7/60 |

FOREIGN PATENT DOCUMENTS

| | | |
|---|---|---|
| JP | 11-38324 A | 2/1999 |
| JP | 4937457 B2 | 5/2012 |
| JP | 2015-82095 A | 4/2015 |
| JP | 2015-82096 A | 4/2015 |
| JP | 2015-108534 A | 6/2015 |
| JP | 2015-108837 A | 6/2015 |
| JP | 2015-156011 A | 8/2015 |
| JP | 2015-166829 A | 9/2015 |
| JP | 2016-75817 A | 5/2016 |
| JP | 2016-212190 A | 12/2016 |
| WO | WO 2008/028745 A1 | 3/2008 |
| WO | WO 2015/089564 A1 | 6/2015 |
| WO | WO 2015/107872 A1 | 7/2015 |

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2016/086085, dated Sep. 13, 2018, with English Translation of the Written Opinion.
International Search Report (form PCT/ISA/210) for International Application No. PCT/JP2016/086085, dated Mar. 7, 2017, with English Translation.
Japanese Office Action for Japanese Application No. 2016-037697, dated Sep. 25, 2018, with English translation.
Extended European Search Report, dated Mar. 18, 2019, for European Application No. 16892715.0.

* cited by examiner

FIG. 2
| TYPE OF CELL | CULTURE PERIOD | CULTURE CONDITION | INITIAL SCANNING RANGE |
|---|---|---|---|
| S1 | T1 | CONDITION 1 | R1 |
| S2 | T2 | CONDITION 2 | R2 |
| S3 | T3 | CONDITION 3 | R3 |
| ⋮ | ⋮ | ⋮ | ⋮ |
FIG. 3
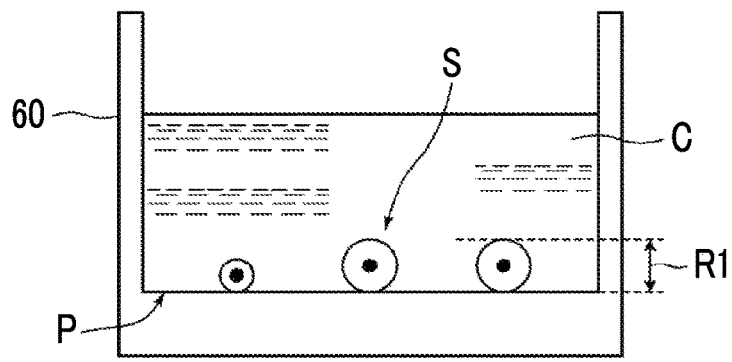
FIG. 4
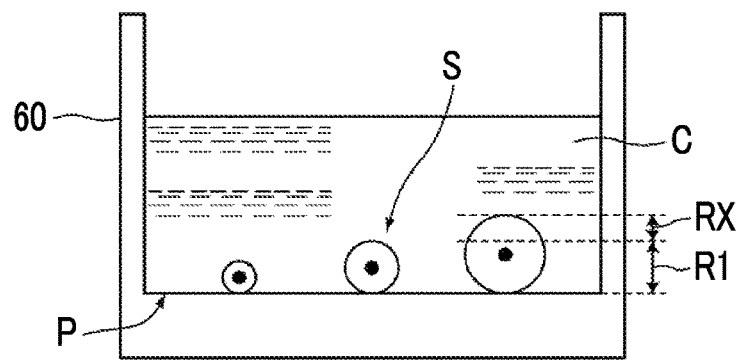

CELL OBSERVATION APPARATUS AND METHOD

CROSS-REFERENCE TO RELATED APPLICATIONS

This application is a Continuation of PCT International Application No. PCT/JP2016/086085 filed on Dec. 5, 2016, which claims priority under 35 U.S.C § 119(a) to Japanese Patent Application No. 2016-037697 filed on Feb. 29, 2016. Each of the above application(s) is hereby expressly incorporated by reference, in its entirety, into the present application.

BACKGROUND OF THE INVENTION

1. Field of the Invention

The present invention relates to a cell observation apparatus and method for forming an image of a cultured cell by an image formation optical system and observing the image.

2. Description of the Related Art

In recent years, various microscopes including phase contrast microscopes have been widely used as microscopes for observing a cultured cell such as a stem cell.

Although it is known that, in the process of cell growth, cells are stacked in three dimensions, it is difficult to observe the three-dimensional structure of the stacked cells at once because an objective lens of a microscope has a focal depth.

In JP2015-166829A, it is proposed to perform autofocus control based on a parameter determined according to the growth degree of cells in a thickness direction, and then perform imaging according to the cell thickness through the autofocus control.

In addition, in JP2015-108534A, a method of capturing images of a plurality of cells disposed three-dimensionally to be spaced from each other, and a method of moving a focusing position of an objective lens at a preset pitch in a direction of the optical axis and combining images captured at respective focusing positions are proposed.

In addition, in JP4937457B, it is proposed that, in a case where a thick cell is observed while moving the focusing position of the objective lens in a direction of the optical axis, a thickness of a cell is estimated and a scanning range of the focusing position is determined based on the estimated thickness.

SUMMARY OF THE INVENTION

However, in the method disclosed in JP2015-166829A, since the focal position finally determined by the autofocus control is at one position, it is not possible to observe the three-dimensional structure of the stacked cells.

In addition, in JP2015-108534A, merely a method of imaging a plurality of cells disposed three-dimensionally to be spaced from each other is disclosed, and a method of imaging thick cells is not proposed at all.

In addition, in JP4937457B, it is proposed that the scanning range of the focusing position is determined based on the size of the cell that is set and input by a user, but there is a possibility of a difference between the size of the cell that is set and input and the size of the actually cultured cell. For example, in a case where the scanning range is too wide for the size of the actually cultured cell, unnecessary imaging is performed. On the other hand, in a case where the scanning range is too narrow, insufficient imaging occurs in the thickness direction of the cell.

In view of the above problem, an object of the present invention is to provide a cell observation apparatus and method capable of observing a three-dimensional structure of an entire cell and preventing unnecessary imaging.

A cell observation apparatus according to an aspect of the present invention comprises: an image formation optical system that forms an image of a cell cultured in a culture vessel; an image formation optical system control unit that controls a scanning range of a focal position of the image formation optical system; a thickness information acquisition unit that acquires information relating to a thickness of the cell from a placement surface in the culture vessel; and an imaging unit that receives the image formed by the image formation optical system and captures an image of the cell. The image formation optical system control unit sets an initial scanning range of the focal position for the cell based on the information relating to the thickness, controls the image formation optical system to form an image of the cell at each of a plurality of the focal positions within the set initial scanning range, subsequently acquires the image captured by the imaging unit for each of the plurality of focal positions, estimates the thickness of the cell based on the acquired image, updates the initial scanning range of the focal position based on the estimated thickness of the cell, and controls the image formation optical system to form an image of the cell at each of a plurality of focal positions within the updated scanning range.

In the cell observation apparatus according to the aspect of the present invention, it is desirable that the image formation optical system control unit determines whether or not an entire cell has been imaged in a thickness direction of the cell based on the image for each of the plurality of focal positions, estimates the thickness of the cell in a case where it is determined that the entire cell has not been imaged, and updates the initial scanning range of the focal position based on the estimated thickness of the cell.

Further, in the cell observation apparatus according to the aspect of the present invention, in a case where it is determined that the entire cell has not been imaged in the thickness direction of the cell, the image formation optical system control unit may update an unimaged range as a new scanning range of the focal position.

Further, in the cell observation apparatus according to the aspect of the present invention, the image formation optical system control unit may determine whether or not the entire cell has been imaged in the thickness direction of the cell based on edge information of the image for each focal position.

Further, in the cell observation apparatus according to the aspect of the present invention, in a case where an edge of the cell does not exist in the image for the focal position farthest away from the placement surface of the cell, the image formation optical system control unit may determine that the entire cell has been imaged in the thickness direction of the cell.

Further, in the cell observation apparatus according to the aspect of the present invention, the image formation optical system control unit may set an initial scanning range of the focal position at a next capturing time point of the cell based on the images of the cell captured at different time points in the past.

Further, in the cell observation apparatus according to the aspect of the present invention, the thickness information acquisition unit may acquire at least one of a cell type, a cell culture period, a cell culture condition, or a cell size as the information relating to the thickness.

Further, in the cell observation apparatus according to the aspect of the present invention, the image formation optical system control unit may form an image of the cell at each of three or more focal positions within the initial scanning range set based on the information relating to the thickness.

Further, the cell observation apparatus according to the aspect of the present invention may further comprise an illumination light irradiation unit that irradiates the cell with illumination light for phase difference measurement. The image formation optical system may form a phase difference image of the cells.

A cell observation method according to another aspect of the present invention is a method for forming an image of a cell cultured in a culture vessel by using an image formation optical system and observing the formed image, the method comprising: acquiring information relating to a thickness of the cell from a placement surface in the culture vessel; setting an initial scanning range of a focal position for the cell based on the acquired information relating to the thickness, and controlling the image formation optical system to form an image of the cell at each of a plurality of focal positions within the set initial scanning range to be captured; and subsequently acquiring the image captured for each of the plurality of focal positions, estimating a thickness of the cell based on the acquired image, updating an initial scanning range of the focal position based on the estimated cell thickness, and forming an image of the cell at each of a plurality of focal positions within the updated scanning range.

According to the cell observation apparatus and method of the aspects of present invention, information relating to the thickness of the cell is acquired and an initial scanning range of the focal position for the cell is set based on the acquired information relating to the thickness. By setting the initial scanning range in this way, the scanning range can be narrowed down according to the thickness of the cell, and it is possible to prevent unnecessary imaging.

Then, images of cells are formed and captured, respectively, at a plurality of focal positions within the initial scanning range, captured images for each of the plurality of focal positions are acquired, and based on the acquired images, a cell thickness is estimated. Thus, it is possible to estimate the thickness of actually cultured cells.

Then, based on the estimated cell thickness, the initial scanning range of the focal position is updated and images of the cells at the plurality of focal positions within the updated scanning range are respectively formed. Therefore, it is possible to observe a three-dimensional structure of the entire cell and to prevent unnecessary imaging.

BRIEF DESCRIPTION OF THE DRAWINGS

FIG. 2 is a diagram showing an example of a table in which types of culture vessels, culture periods, and culture conditions are associated with initial scanning ranges.

FIG. 3 is a diagram illustrating setting of the initial scanning range.

FIG. 4 is a diagram illustrating update of the initial scanning range.

DESCRIPTION OF THE PREFERRED EMBODIMENTS

Figure 1:
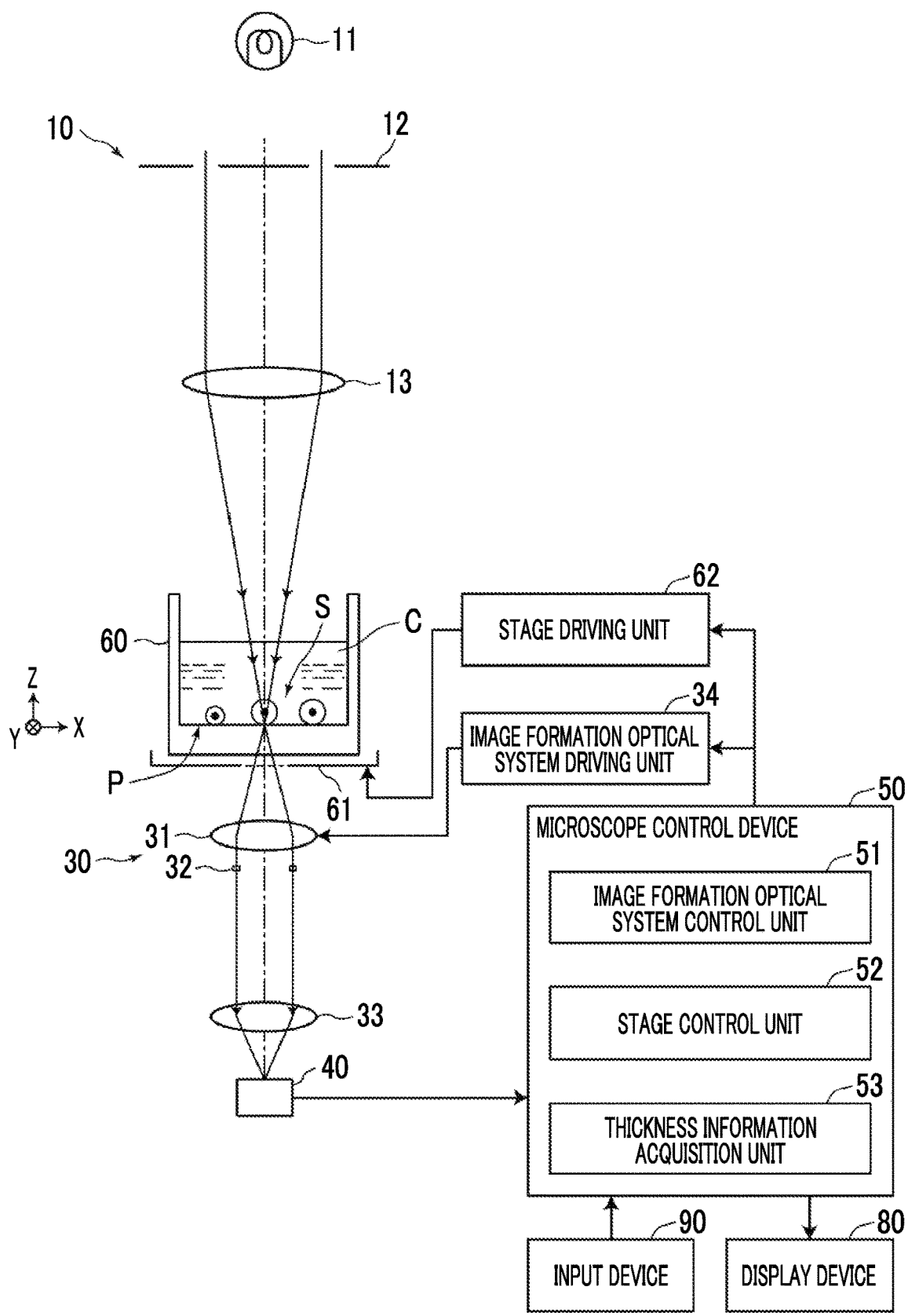
FIG. 1 is a diagram showing a schematic configuration of a microscope system using one embodiment of a cell observation apparatus of the present invention.

Hereinafter, a microscope system using one embodiment of a cell observation apparatus and method of the present invention will be described in detail with reference to the drawings. FIG. 1 is a diagram showing a schematic configuration of a microscope system according to the present embodiment.

As shown in FIG. 1, the microscope system of the present embodiment includes an illumination light irradiation unit 10, an image formation optical system 30, an imaging unit 40, a microscope control device 50, a display device 80, and an input device 90.

In the microscope system of the present embodiment, a stage 61 is provided between the illumination light irradiation unit 10 and the image formation optical system 30, and a culture vessel 60 is placed on the stage 61 and supported by the stage 61. In the culture vessel 60, a culture solution C and an observation target S are contained.

The microscope system of the present embodiment includes a stage driving unit 62 that moves the stage 61 in an X direction, a Y direction, and a Z direction. The X direction and the Y direction are directions orthogonal to each other on a plane parallel to a placement surface P of the observation target S, and the Z direction is a direction orthogonal to both the X direction and the Y direction.

In the microscope system of the present embodiment, a main body of a phase contrast microscope is configured with the illumination light irradiation unit 10, the image formation optical system 30, the imaging unit 40, the stage 61, the stage driving unit 62, and an image formation optical system driving unit 34, and the microscope control device 50 controls the main body of the phase contrast microscope. In the present embodiment, the cell observation apparatus of the present invention is configured with the main body of the phase contrast microscope, and an image formation optical system control unit 51 and a thickness information acquisition unit 53 in the microscope control device 50, which will be described later. Hereinafter, a specific configuration of the main body of the phase contrast microscope will be described.

The illumination light irradiation unit 10 irradiates the observation target S contained in the culture vessel 60 with so called illumination light for phase difference measurement, and in the present embodiment, do the irradiation with ring-shaped illumination light as the illumination light for phase difference measurement. Specifically, the illumination light irradiation unit 10 of the present embodiment includes a white light source 11 that emits white light for phase difference measurement, a slit plate 12 having a ring-shaped slit, which allows the white light emitted from the white light source 11 to be incident on the slit plate 12 and be emitted as the ring-shaped illumination light, and a condenser lens 13 on which the ring-shaped illumination light emitted from the slit plate 12 is incident and which irradiates the observation target S with the incident ring-shaped illumination light.

The slit plate 12 is provided with the ring-shaped slit through which the white light passes in a light screen that shields the white light emitted from the white light source 11, and, as the white light passes through the slit, the ring-shaped illumination light is formed.

In the present embodiment, the ring-shaped illumination light is formed by using the slit plate 12 as described above. However, the method for forming the ring-shaped illumination light is not limited thereto, and for example, the ring-shaped illumination light may be formed by using a spatial light modulation element or the like.

In the present embodiment, the ring-shaped illumination light is used as the illumination light for phase difference measurement, but illumination light having a shape other than the ring shape may be used, and as long as the illumination light has a shape that is conjugated with a phase plate 32, which will be described later, other shapes such as a triangular shape and a quadrangular shape may be used.

In the culture vessel 60 installed on the stage 61, cells to be cultured are disposed as observation targets S. Examples of the cells to be cultured include pluripotent stem cells such as induced pluripotent stem (iPS) cells and embryonic stem (ES) cells, cells of a nerve, skin, cardiac muscle, and a liver differentiated and induced from stem cells, cells of skin, a retina, myocardium, a blood corpuscle, a nerve, and an organ extracted from a human body, and the like. In the present specification, in a case of referring to the cell, it means not only a single cell but also a cell group (a cell colony) in which a plurality of cells are aggregated. Further, in the present embodiment, a boundary surface between a bottom portion of the culture vessel 60 and the observation target S is referred to as the placement surface P of the observation target S. As the culture vessel 60, a petri dish, a well plate in which a plurality of wells are arranged, or the like can be used. In the case of the well plate, the observation target S and the culture solution C are contained in each well.

The image formation optical system 30 forms an image of the observation target S in the culture vessel 60 on the imaging unit 40, and includes an objective lens 31, a phase plate 32, and an image formation lens 33.

The phase plate 32 is a plate where a phase ring is formed on a transparent plate transparent to the wavelength of the ring-shaped illumination light. The size of the slit of the slit plate 12 described above has a conjugate relationship with the phase ring.

The phase ring has a ring shape with a phase film that shifts a phase of incident light by a quarter wavelength and a light attenuation filter that attenuates the incident light. As the direct light incident on the phase plate 32 passes through the phase ring, the phase is shifted by a quarter wavelength and the brightness of the light is weakened. On the other hand, most of diffracted light diffracted by the observation target S passes through the transparent plate portion of the phase plate 32, and the phase and the brightness of the light do not change.

The image formation lens 33 allows direct light and diffracted light having passed through the phase plate 32 to be incident, and forms an image of the two types of light on the imaging unit 40.

The image formation optical system driving unit 34 is provided with a mechanism that moves the objective lens 31 in the Z direction shown in FIG. 1 based on the control signal output from the image formation optical system control unit 51, which will be described later, and the focal position of the image formation optical system 30 is changed by the movement of the objective lens 31 caused by the image formation optical system driving unit 34.

The image formation optical system 30 may be configured such that an optical magnification can be changed. As an example of a method for changing the optical magnification, a plurality of objective lenses 31 having mutually different magnifications may be provided in the image formation optical system 30, and the plurality of objective lenses 31 may be automatically switched. In this case, the phase plate 32 is also changed in accordance with the change of the objective lens 31. Alternatively, the optical magnification may be changed by manual exchanging of the objective lens 31 by the user.

The imaging unit 40 includes an imaging element that receives the image of the observation target S formed by the image formation lens 33 and captures the phase difference image of the observation target S. As the imaging element, a charge-coupled device (CCD) image sensor, a complementary metal-oxide semiconductor (CMOS) image sensor, or the like can be used.

The microscope control device 50 is configured with a computer having a central processing unit (CPU), a semiconductor memory, a hard disk, and the like.

The microscope control device 50 controls the operation of the entire main body of the phase contrast microscope, and specifically, as shown in FIG. 1, includes an image formation optical system control unit 51 that controls the image formation optical system driving unit 34, a stage control unit 52 that controls the stage driving unit 62, and a thickness information acquisition unit 53.

The image formation optical system control unit 51 controls the image formation optical system driving unit 34 to move the objective lens 31 in the Z direction, thereby changing the focal position of the image formation optical system 30. In a case of capturing the phase difference image of the observation target S, the image formation optical system control unit 51 according to the present embodiment sets a plurality of focal positions in the Z direction and captures a phase difference image for each focal position. As a result, it is possible to capture a plurality of phase difference images in the thickness direction of the observation target S, and it is possible to observe the three-dimensional structure of the observation target S. The thickness of the observation target S refers to the thickness of the observation target S (cell) from the placement surface P of the culture vessel 60.

Further, based on the information relating to the thickness of the observation target S acquired by the thickness information acquisition unit 53, the image formation optical system control unit 51 sets an initial scanning range and an initial scanning pitch of focal positions for the observation target S. Then, by controlling the image formation optical system 30, images of the observation target S at a plurality of focal positions within the set initial scanning range are formed, respectively. The initial scanning pitch is a distance between a plurality of focal positions within the initial scanning range. It is desirable that the number of focal positions within the initial scanning range is at least three or more. The setting of the initial scanning range based on the information relating to the thickness of the observation target S will be described in detail later.

The stage control unit 52 drives and controls the stage driving unit 62, thereby moving the stage 61 in the X direction, the Y direction, and the Z direction. Since the stage 61 is moved in the X direction and the Y direction, for example, the interior of one cell is scanned with the illumination light for a phase difference measurement, and a phase difference image for each of a plurality of imaging regions (visual fields) divided within one cell is captured.

The thickness information acquisition unit 53 acquires information relating to the thickness of the observation target S (cell). Examples of the information relating to the thickness include information on a type of the cell, information on a culture period of the cell, information on a culture condition of the cell, information on the size of the cell, and the like. In the present embodiment, information on the type of the cell, information on the culture period of the cell, and information on the culture condition of the cell are acquired. The information on the size of the cell is information indicating the size of the cell in the X-Y direction.

In addition, the information on the type of the cell is information indicating a type of the cell as a culture object, such as the pluripotent stem cell, the differentiated and induced nerve cell and the differentiated and induced skin cell as described above. The information on the type of the cell may be set and input using the input device 90 by a user, or may be acquired, for example, by providing a recording medium such as a barcode or an integrated circuit (IC) chip in which the information on the type of the cell is recorded in the culture vessel 60, and reading out from the recording medium.

In addition, the information on the culture period of the cell is information indicating a period of time from the start of the culture of the cell, or a period of time elapsed since the addition of the drug or the like to the cell to be cultured. The information on the culture period of the cell may be set and input using the input device 90 by a user, or may be automatically measured by providing a timer or the like.

Further, examples of the information on the culture condition of the cell include information such as a type of the culture solution C (medium), a type and amount of a growth factor, and a type and amount of a drug to be added, but any condition that influences the growth rate of the cell may be used as well. The information on the culture condition of the cell may also be set and input using the input device 90 by a user or may be acquired, for example, by providing a recording medium such as a barcode or an integrated circuit (IC) chip in which the information on the culture condition of the cell is recorded in the culture vessel 60, and reading out from the recording medium.

The information on the type of the cell, the information on the culture period, and the information on the culture condition acquired by the thickness information acquisition unit 53 are acquired by the image formation optical system control unit 51. As shown in FIG. 2, in the image formation optical system control unit 51, a table is set in advance, in which the information on the type of the cell, the information on the culture period, and the information on the culture condition are associated with information on the initial scanning range of the focal position of the image formation optical system 30.

The image formation optical system control unit 51 sets the initial scanning range of the focal position of the image formation optical system 30, based on the acquired information on the type of the cell, information on the culture period, and information on the culture condition, with reference to the table shown in FIG. 2. Then, the image formation optical system control unit 51 controls the image formation optical system 30 to focus on a plurality of focal positions within the initial scanning range, at each of which an image of the observation target S is formed. In the present embodiment, the initial scanning pitch is set to be a fixed value. However, the initial scanning pitch may also be changed based on the information relating to the thickness. For example, as the cell thickness increases, the initial scanning pitch may be increased. In this case, the initial scanning pitch may be set such that the number of a plurality of focal positions within the initial scanning range is always the same. That is, the number of phase difference images that are captured for the observation target S may always be the same.

Further, in a case of acquiring the information on the size of the cell as the information relating to the thickness of the observation target S, a table in which the cell size and the initial scanning range are associated with each other may be set in advance. For example, the information on the size of the cell may be set and input using the input device 90 by a user.

As described above, the image formation optical system control unit 51 sets the initial scanning range of the focal position of the image formation optical system 30 based on the information relating to the thickness of the observation target S, thereby, for example, as shown in FIG. 3, making it possible to set an initial scanning range R1 according to the thickness of the observation target S. Thus, it is possible to capture a plurality of phase difference images over the entire observation target S in the thickness direction, and to suppress wasteful capturing of the phase difference image.

Here, since the information relating to the thickness is not information obtained by directly measuring the thickness of the observation target S, and is merely the information indirectly indicating the thickness of the observation target S, as shown in FIG. 3, the actual thickness of the observation target S and the initial scanning range R1 are not necessarily equal in magnitude and may have different sizes. That is, there is a possibility that the relationship between the thickness of the observation target S and the initial scanning range R1 may be as shown in FIG. 4.

In this case, although it is possible to capture the phase difference image in the range of the observation target S corresponding to the initial scanning range R1, in the range of RX shown in FIG. 4, it is not possible to capture the phase difference image of the observation target S. As a result, it is not possible to capture the phase difference image over the entire observation target S in the thickness direction, and it is not possible to observe the structure or the like of the observation target S in the range of RX. For example, in a case where there are a plurality of cells as the observation target S, the entire observation target S mentioned herein includes all of the plurality of cells.

Therefore, the image formation optical system control unit 51 acquires a phase difference image captured for each focal position by scanning the focal positions within the initial scanning range R1, and based on the acquired phase difference image, determines whether or not the phase difference images are captured over the entire observation target S. In a case where phase difference images are not captured over the entire observation target S, the image formation optical system control unit 51 estimates the thickness of the observation target S based on the phase difference image for each focal position, and updates the initial scanning range of the focal positions based on the estimated thickness of the observation target S. Hereinafter, a method of determining whether or not phase difference images are captured over the entire observation target S and estimating the thickness of the observation target S will be described in detail.

First, the image formation optical system control unit 51 extracts an edge of a cell included in a phase difference image for each focal position. Known image processing can be used as a method of extracting the edge of the cell included in the phase difference image. Then, the image formation optical system control unit 51 plots the edge amount of the phase difference image at each focal position, with the horizontal axis representing the focal position (Z direction) of each phase difference image and the vertical axis representing the amount of edge of each phase difference image, and performs an interpolation operation, or the like, to acquire an profile of the edge amount as shown by a solid line in FIG. 5. The positive direction (the right direction on the drawing) on the horizontal axis in FIG. 5 is a direction away from the placement surface P of the observation target S.

Figure 5:
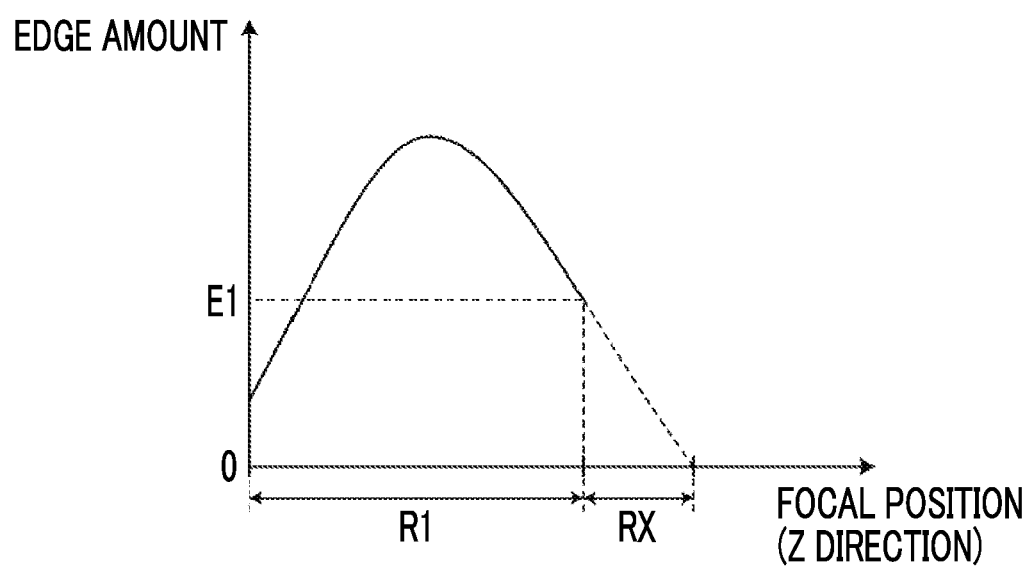
FIG. 5 is a graph illustrating estimation of cell thickness.

Here, in a case where the relationship between the actual thickness of the observation target S and the initial scanning range R1 is, for example, the relationship as shown in FIG. 4, that is, in the case where the actual thickness of the observation target S is larger than the initial scanning range R1, the profile of the edge amount is a profile as shown by the solid line in FIG. 5. That is, the profile of the edge amount does not converge to zero, and is created up to the position of an edge amount E1. The edge amount E1 is the edge amount of the phase difference image at the focal position farthest away from the placement surface of the observation target S within the initial scanning range R1.

As described above, in a case where the profile of the edge amount does not converge to zero, the image formation optical system control unit 51 determines that phase difference images are not captured over the entire observation target S. Here, with the profile that is converged to zero as shown by the dotted line in FIG. 5, which is drawn by performing extrapolation or the like, the range up to the focal position where the edge amount converges to zero is estimated as the thickness of the observation target S. That is, in the case of the profile as shown in FIG. 5, the range obtained by adding RX to the initial scanning range R1 is estimated as the thickness of the observation target S.

Then, the image formation optical system control unit 51 updates the scanning range of the focal position from R1 to RX, and controls the image formation optical system 30 to capture the phase difference image in the range (the range of RX shown in FIG. 4) that was not captured in the previous capturing of the phase difference image. In a case where the profile of the edge amount converges to zero, that is, in the case where no edge of the cell is present within the phase difference image of the focal position farthest away from the placement surface P of the observation target S within the initial scanning range R1, the image formation optical system control unit 51 determines that phase difference images are captured over the entire observation target S, and no further phase difference image is captured.

In a case where there are a plurality of cells as the observation target S, determination may be made whether or not phase difference images for each cell is captured over the entire cell. Then, estimation of the thickness is performed only on the cell, over the entirety of which phase difference images are not captured, and the image formation optical system 30 and the stage driving unit 62 may be controlled so that phase difference images of an un-imaged range of the cell are captured.

Returning to FIG. 1, the microscope control device 50 is connected to an input device 90 and a display device 80. The input device 90 is provided with an input device such as a keyboard or a mouse and receives setting inputs by a user. In particular, the input device 90 according to the present embodiment receives setting inputs such as the above-described information on the type of the cell, the information on the culture period and the information on the culture condition.

The display device 80 is configured with a display device such as a liquid crystal display and displays the phase difference image and the like captured by the imaging unit 40. Note that the display device 80 may be configured with a touch panel such that the display device 80 can also function as the input device 90.

Figure 6:
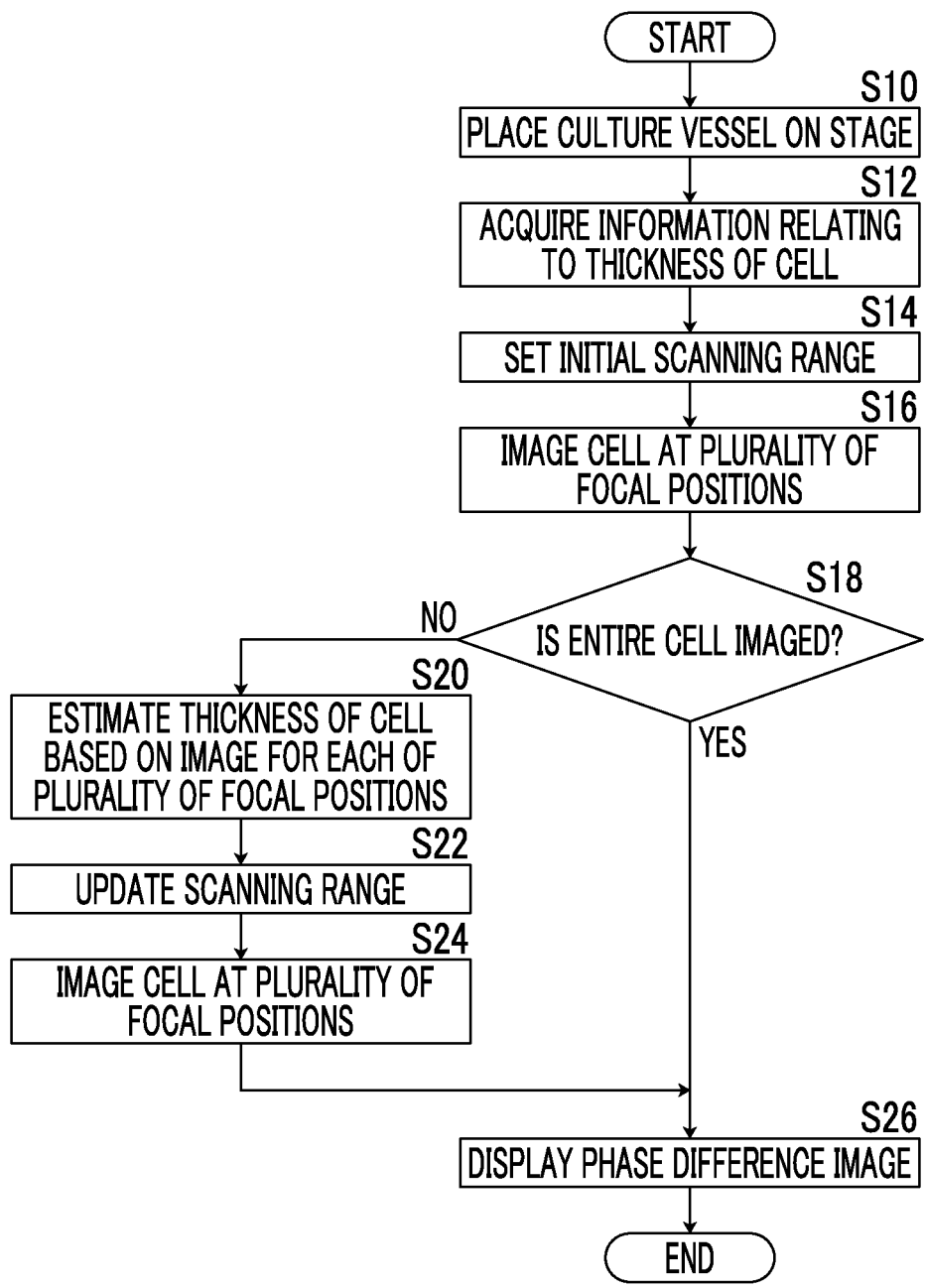
FIG. 6 is a flowchart illustrating an operation of the microscope system using the embodiment of the cell observation apparatus of the present invention.

Next, the operation of the microscope system of the present embodiment will be described with reference to a flowchart shown in FIG. 6.

First, the culture vessel 60 containing the observation target S is placed on the stage 61 (S10). Then, information relating to the thickness of the cell, such as the information on the type of the cell, the information on the culture period, and the information on the culture condition, is acquired by setting inputs by the user (S12).

The information on the type of the cell, the information on the culture period and the information on the culture condition are acquired by the image formation optical system control unit 51, and the image formation optical system control unit 51 sets the initial scanning range of the focal positions of the image formation optical system 30 based on the information (S14).

Then, the culture vessel 60 is irradiated with ring-shaped illumination light from the illumination light irradiation unit 10, the focal positions of the image formation optical system 30 are scanned within the initial scanning range, and the phase difference image of the observation target S is captured for each focal position (S16).

The phase difference image for each focal position is acquired by the image formation optical system control unit 51, and the image formation optical system control unit 51 determines, based on the acquired plurality of phase difference images, whether or not the phase difference images are captured over the entire observation target S (S18).

In a case where the image formation optical system control unit 51 determines that phase difference images are not captured over the entire the observation target S, the image formation optical system control unit 51 estimates the thickness of the observation target S based on the phase difference image for each focal position (S20), and updates the initial scanning range of the focal positions based on the estimated thickness of the observation target S (S22).

Then, the focal positions of the image formation optical system 30 are scanned within the updated scanning range, the phase difference image of the observation target S is captured for each focal position, and a phase difference image in the range that was not captured in the previous capturing of the phase difference image is acquired (S24).

On the other hand, in a case where it is determined that phase difference images are captured over the entire observation target S in S18, no further phase difference image is captured.

The phase difference image for each focal position of the observation target S captured as described above is output to the display device 80 and is displayed (S26). In a case of displaying the phase difference image for each focal position, the phase difference images may be sequentially switched for display, or may be displayed side by side.

According to the microscope system of the above embodiment, information relating to the thickness of the cell is acquired, and the initial scanning range of the focal positions for the cell is set based on the acquired information relating to the thickness. By setting the initial scanning range as described above, it is possible to reduce the scanning range depending on the thickness of the cell, and to prevent unnecessary imaging.

Then, the images of the cell at the plurality of focal positions within the initial scanning range are formed and captured, then the phase difference image captured for each of the plurality of focal positions is acquired, and the cell thickness is estimated based on the acquired phase difference images. Accordingly, it is possible to estimate the thickness of the actually cultured cell.

Then, the initial scanning range of the focal positions is updated based on the estimated thickness of the cell, and the images of the cell at the plurality of focal positions within the updated scanning range are respectively formed. Therefore, it is possible to observe the three-dimensional structure of the entire cell and to prevent unnecessary imaging.

In the case of performing time lapse imaging, for example, using the microscope system according to the above embodiment, at each capturing time point of the phase difference image, the initial scanning range may be set based on the information relating to the cell thickness as described above, but the present invention is not limited thereto. For example, at the third capturing time point and subsequent capturing time points, the initial scanning range may be set based on the phase difference image captured at least previous two capturing time points.

Figure 7:
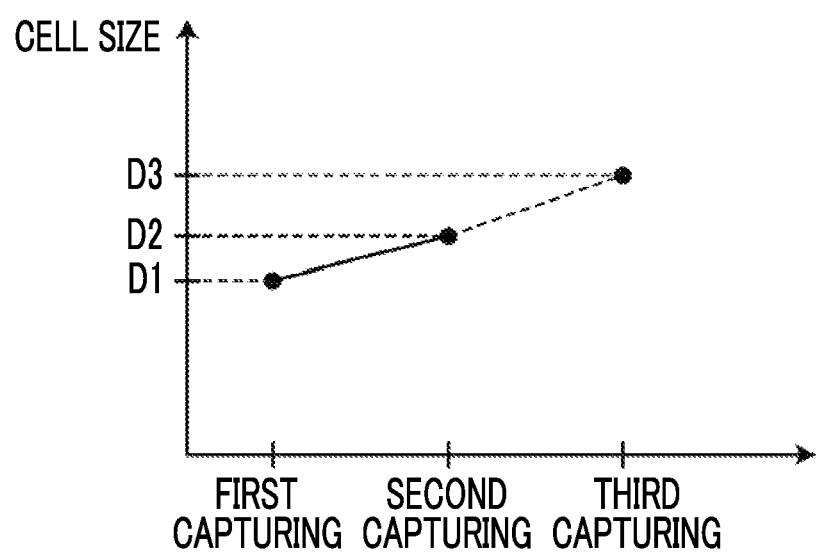
FIG. 7 is a graph illustrating a method of setting an initial scanning range based on past images.

Specifically, for example, as shown in FIG. 7, the image formation optical system control unit 51 calculates a cell size D1 included in the phase difference image acquired by the first capturing, and a cell size D2 included in the phase difference image acquired by the second capturing, and for example, extrapolation is performed to estimate a cell size D3 at the third capturing time point based on information on the sizes of the cells. Based on the cell size D3 at the third capturing time point, the thickness of the cell may be estimated, and based on the estimated thickness, the initial scanning range may be set.

In this case, the initial scanning pitch may be set according to the thickness of the cell as in the above-described embodiment. Further, the process described above is not limited to the third capturing time point, and also possible at the fourth capturing time point and subsequent capturing time points, that is, the size of the cell at the fourth capturing time point and subsequent capturing time points is estimated in a similar manner, and the cell thickness may be estimated based on the size of the cell.

Further, the relationship between the cell size and the cell thickness may be set in advance using a lookup table, a function, or the like. In addition, such a lookup table or function may be set for each type of cell, for each culture period, or for each culture condition.

Further, in the above embodiment, the initial scanning range and the initial scanning pitch may be changed according to the magnification of the objective lens 31 to be used and/or the wavelength of the illumination light. Specifically, since the depth of field becomes shallower as the magnification of the objective lens is higher, the initial scanning range and the initial scanning pitch may be narrowed. In addition, since the depth of field becomes shallower as the wavelength of the illumination light is shorter, the initial scanning range and the initial scanning pitch may be narrowed.

In the above-described embodiment, the present invention is applied to a phase contrast microscope. However, the present invention is not limited to the phase contrast microscope, and may be applied to other microscopes such as a differential interference microscope and a bright field microscope.

EXPLANATION OF REFERENCES

10: illumination light irradiation unit
11: white light source
12: slit plate
13: condenser lens
30: image formation optical system
31: objective lens
32: phase plate
33: image formation lens
34: image formation optical system driving unit
40: imaging unit
50: microscope control device
51: image formation optical system control unit
52: stage control unit
53: thickness information acquisition unit
60: culture vessel
61: stage
62: stage driving unit
80: display device
90: input device
C: culture solution
P: placement surface
R1: initial scanning range
RX: scanning range
S: observation target

What is claimed is:

1. A cell observation apparatus comprising:
an image formation optical system that forms an image of a cell cultured in a culture vessel;
an imaging unit that receives the image formed by the image formation optical system and captures the image of the cell; and
a processor configured to control a scanning range of a focal position of the image formation optical system and acquire information relating to a thickness of the cell from a placement surface in the culture vessel;
wherein the processor is further configured to
set an initial scanning range of the focal position for the cell based on the information relating to the thickness;
control the image formation optical system to form an image of the cell at each of a plurality of the focal positions within the set initial scanning range;
subsequently acquire the image captured by the imaging unit for each of the plurality of focal positions;
estimate the thickness of the cell based on the acquired image;
update a scanning range of the focal position initially set to be positioned within a range of the estimated thickness of the cell excluding the scanning range initially set in a thickness direction of the cell;
control the image formation optical system to form an image of the cell at each of the plurality of focal positions within the updated scanning range; and
acquire the image captured by the imaging unit for each of the plurality of focal positions within the updated scanning range.

2. The cell observation apparatus according to claim 1, wherein the processor is further configured to
determine whether or not an entire cell has been imaged in a thickness direction of the cell based on the image for each of the plurality of focal positions;
estimate the thickness of the cell in a case where it is determined that the entire cell has not been imaged; and
update the initial scanning range of the focal position based on the estimated thickness of the cell.

3. The cell observation apparatus according to claim 2, wherein in a case where it is determined that the entire cell has not been imaged in the thickness direction of the cell, the processor is further configured to update an unimaged range as a new scanning range of the focal position.

4. The cell observation apparatus according to claim 2, wherein the processor is further configured to determine whether or not the entire cell has been imaged in the thickness direction of the cell based on edge information of the image for each focal position.

5. The cell observation apparatus according to claim 3, wherein the processor is further configured to determine whether or not the entire cell has been imaged in the thickness direction of the cell based on edge information of the image for each focal position.

6. The cell observation apparatus according to claim 4, wherein in a case where an edge of the cell does not exist in the image for the focal position farthest away from the placement surface of the cell, the processor is further configured to determine that the entire cell has been imaged in the thickness direction of the cell.

7. The cell observation apparatus according to claim 5, wherein in a case where an edge of the cell does not exist in the image for the focal position farthest away from the placement surface of the cell, the processor is further configured to determine that the entire cell has been imaged in the thickness direction of the cell.

8. The cell observation apparatus according to claim 1, wherein the processor is further configured to set the initial scanning range of the focal position at a next capturing time point of the cell based on the images of the cell captured at different time points in the past.

9. The cell observation apparatus according to claim 2, wherein the processor is further configured to set the initial scanning range of the focal position at a next capturing time point of the cell based on the images of the cell captured at different time points in the past.

10. The cell observation apparatus according to claim 3, wherein the processor is further configured to set the initial scanning range of the focal position at a next capturing time point of the cell based on the images of the cell captured at different time points in the past.

11. The cell observation apparatus according to claim 4, wherein the processor is further configured to set the initial scanning range of the focal position at a next capturing time point of the cell based on the images of the cell captured at different time points in the past.

12. The cell observation apparatus according to claim 5, wherein the processor is further configured to set the initial scanning range of the focal position at a next capturing time point of the cell based on the images of the cell captured at different time points in the past.

13. The cell observation apparatus according to claim 6, wherein the processor is further configured to set the initial scanning range of the focal position at a next capturing time point of the cell based on the images of the cell captured at different time points in the past.

14. The cell observation apparatus according to claim 7, wherein the processor is further configured to set the initial scanning range of the focal position at a next capturing time point of the cell based on the images of the cell captured at different time points in the past.

15. The cell observation apparatus according to claim 1, wherein the processor is further configured to acquire at least one of a cell type, a cell culture period, a cell culture condition, or a cell size as the information relating to the thickness.

16. The cell observation apparatus according to claim 2, wherein the processor is further configured to acquire at least one of a cell type, a cell culture period, a cell culture condition, or a cell size as the information relating to the thickness.

17. The cell observation apparatus according to claim 3, wherein the processor is further configured to acquire at least one of a cell type, a cell culture period, a cell culture condition, or a cell size as the information relating to the thickness.

18. The cell observation apparatus according to claim 1, wherein the processor is further configured to form an image of the cell at each of three or more focal positions within the initial scanning range set based on the information relating to the thickness.

19. The cell observation apparatus according to claim 1, further comprising:
an illumination light irradiation unit that irradiates the cell with illumination light for phase difference measurement,
wherein the image formation optical system forms a phase difference image of the cell.

20. A cell observation method for forming an image of a cell cultured in a culture vessel by using an image formation optical system and observing the formed image, the method comprising:
acquiring information relating to a thickness of the cell from a placement surface in the culture vessel;
setting an initial scanning range of a focal position for the cell based on the acquired information relating to the thickness, and controlling the image formation optical system to form an image of the cell at each of a plurality of focal positions within the set initial scanning range to be captured; and
subsequently acquiring the image captured for each of the plurality of focal positions, estimating a thickness of the cell based on the acquired image, updating a scanning range of the focal position initially set to be positioned within a range of the estimated cell thickness excluding the scanning range initially set in a thickness direction of the cell, forming an image of the cell at each of a plurality of focal positions within the updated scanning range; and acquiring the image captured by the image formation optical system for each of the plurality of focal positions within the updated scanning range.

21. The cell observation apparatus according to claim 1, wherein the processor is further configured to update the scanning range of the focal position initially set to be positioned within the range of the estimated thickness of the cell excluding the scanning range initially set in the thickness direction of the cell, in a case where it is determined that the entire cell is not captured by the initial scanning range.

* * * * *